United States Patent [19]
Saitoh et al.

[11] Patent Number: 4,914,140
[45] Date of Patent: * Apr. 3, 1990

[54] ACRYLIC COPOLYMER AND SKIN PROTECTIVE

[75] Inventors: Izumi Saitoh, Hyogo; Shigeru Kido, Osaka; Yoshio Sasaki; Syuichiro Shinohara, both of Fukui, all of Japan

[73] Assignees: Shinonogi and Co., Ltd., Osaka; Nisshin Chemical Co., Ltd., Fukui, both of Japan

[*] Notice: The portion of the term of this patent subsequent to Oct. 17, 2006 has been disclaimed.

[21] Appl. No.: 353,818

[22] Filed: May 18, 1989

Related U.S. Application Data

[62] Division of Ser. No. 109,619, Oct. 19, 1987, Pat. No. 4,874,830.

[30] Foreign Application Priority Data

Oct. 23, 1986 [JP] Japan ................................ 61-253071
Oct. 23, 1986 [JP] Japan ................................ 61-253072

[51] Int. Cl.$^4$ .............................................. C08L 15/00
[52] U.S. Cl. .................................. 523/111; 523/105; 526/318.4; 526/936
[58] Field of Search ................................ 523/111, 105

[56] References Cited

U.S. PATENT DOCUMENTS

| 3,501,432 | 3/1970 | Wright et al. | 526/318.4 |
| 3,677,991 | 9/1972 | Moore | 526/318.4 |
| 3,865,904 | 2/1975 | Wingler et al. | 526/318.4 |
| 4,120,841 | 10/1978 | Takahashi et al. | 526/318.4 |
| 4,125,700 | 11/1978 | Graham | 526/318.4 |

FOREIGN PATENT DOCUMENTS

| 46-42024 | 11/1971 | Japan | 526/318.4 |
| 56-145907 | 11/1981 | Japan | 526/318.4 |

Primary Examiner—Joseph L. Schofer
Assistant Examiner—N. Sarofim
Attorney, Agent, or Firm—Wenderoth, Lind & Ponack

[57] ABSTRACT

An acrylic copolymer of ethyl acrylate and methacrylic acid wherein the weight ratio of ethyl acrylate to methacrylic acid is in a range between 75:25 and 95:5, containing therein a residual monomer content of 50 ppm or less, but substantially no surfactants, and which is useful as agents for protecting the skin and manufactured from the following essential components:

a. an acrylic copolymer of ethyl acrylate and methacrylic acid wherein the weight ratio of ethyl acrylate to methacrylic acid is in a range between 75:25 and 95:5, containing therein residual monomers in an amount of 50 ppm or less, but substantially no surfactants—approximately 2 to 10%;
b. cellulose derivative—approximately 0.2 to 2%; and
c. a necessary amount of an aqueous alcohol to make the whole 100%.

17 Claims, No Drawings

ACRYLIC COPOLYMER AND SKIN PROTECTIVE

CROSS-REFERENCE TO RELATED APPLICATION

This is a divisional application of U.S. Application Ser. No. 07/109,619, filed Oct. 19, 1987 now U.S. Pat. No. 4,874,830.

BACKGROUND OF THE INVENTION

1. Field of the Invention

This invention relates to acrylic copolymers with very few impurities and the compositions thereof. The compositions of the acrylic copolymer are applicable onto the surface of the skin and form a very thin but strong film. The skin protective compositions are less irritative to the skin because they contain no surfactants. The thin film, once formed, is resistant to an acidic or neutral environment but easily dissolved in a slightly alkaline environment. In other words, the film is easily washed away by lathering with a toilet soap and water.

2. Prior Arts

Coating compositions which guard the skin from injury by chemicals or other irritants are known. They are designed to protect the skin by a thin film formed on the skin.

Traditionally, cellulose derivatives dissolved in a strong organic solvent such as acetone and ethyl acetate were used, which held such problems that the organic solvent irritated the skin or the mucosa, and that the formed coat film could not be removed easily from the skin.

Recently, a skin protective composed of n-butyl polyester/maleic acid and plasticized ethyl cellulose as main components (hereinafter, sometimes called the protective depending on the prior art) is commercially available in the U.S., but it is not allowed yet in practical use in Japan because it includes some problems in use in that its safety has not been proven.

This protective coating, depending on the prior art, forms a protective film between the skin and extracorporeal catheter, adhesive tape, plaster, diaper or the like. Also, such a usage as to protect the hands from being soiled with grease has been proposed.

The present inventors have strenuously investigated for such a polymer capable of covering the skin of housewives and dishwashers in a restaurant, hospital and a beauty salon who use neutral detergents. Acrylic copolymers have long been practically used in the medical field and are known to have a high safety. But since all the existing acrylic copolymers are manufactured in a routine polymerization, such as solution polymerization and emulsion polymerization, those copolymers are rich in anionic surfactants, chain transfer agents and residual monomers. Accordingly not only are they irritative to the skin and, and introduce problems in environmental protection, but also the coat films become brittle and exhibit waterproof properties when a surfactant exists therein. Hence, these polymers are not suitable in the present invention which aims at providing a film which is impermeable to neutral detergents.

On the other hand, the study of a method to synthesize a copolymer emulsion without using a water-solubilizing agent, such as a surfactant or the equivalent has been continued, but it has been reported that, in the case of polymerizing ethyl acrylate and acrylic acid, for example, that when the quantity of acrylic acid exceeds 2 to 3 molar percent, the formed copolymer emulsion becomes mechanically unstable, which tends to induce gelation (Matsumoto et al.; Kobunshi Ronbunshu, vol. 32, No. 9, 1975).

Moreover, it was made clear that acrylic copolymers already known for pharmaceutical use, for example, represented by Eudragit ® made by R/e,uml/o/ hm Pharma, West Germany, that these copolymers suffer from defects in the elongation and tensile strength.

SUMMARY OF THE INVENTION

The present invention provides skin-protective acrylic copolymers of ethyl acrylate and methacrylic acid wherein the weight ratio of ethyl acrylate to methacrylic acid is in a range between 75:25 and 95:5, which contains therein the residual monomer at amounts of 50 ppm or less, but substantially no surfactant. It provides also skin protective compositions consisting essentially of the following components:

a. An acrylic copolymer of ethyl acrylate and methacrylic acid wherein the weight ratio of ethyl acrylate to methacrylic acid is in a range between 75:25 and 95:5, containing therein the residual monomer at 50 ppm or less but substantially no surfactants—approximately 2 to 10%;

b. An cellulose derivative—approximately 0.2 to 2%; and c. a necessary amount of aqueous alcohol to make the whole 100%.

DESCRIPTION OF THE PREFERRED EMBODIMENT

Problems to be Solved

In order to achieve the purposes of this invention, it is necessary to satisfy the following conditions in good balance, but such a copolymer as to satisfy these conditions simultaneously has not yet been developed. The desired properties of the copolymer as a skin protective in this invention are as follows:

(1) the copolymer is such that a thin coat film can be formed when applied to the skin;

(2) it has water resistance and is soluble in an alkali;

(3) it forms a stretchable pliable film, which adheres tightly to the skin;

(4) it contains few impurities, such as residual monomers, and has neither odor nor irritation to the skin;

(5) neutral detergents can not be passed through such films;

(6) the copolymer is soluble in alcohol or water-containing a alcohol; and (7) the copolymer is permeable to air and to water and also the covered portion does not become stuffy or sticky.

Means to Solve the Problems

The present inventors, considering the above points, found out that a preferable copolymer suitable for this invention can be synthesized by using the monomers comprising 75 to 95 parts by weight of ethyl acrylate (hereinafter occasionally abbreviated as EA) and 25 to 5 parts by weight of methacrylic acid (hereinafter sometimes abbreviated as MAA) in deionized water with persulfate as a polymerization initiator by heating, and if desired, using furthermore a redox catalysts solely or by combining it with such materials as hydrogen peroxide, ferrous sulfate and L-ascorbic acid, and post-treating, to thereby reach the completion of this invention. The monomer unit of copolymer used in this invention is explained further in detail.

Ethyl acrylate is used in the copolymer so as to occupy in a range of 75 to 95 parts by weight, preferably in a range of 80 to 90 parts by weight. The reason why EA is selected is that it can make the synthesized copolymer easily soluble in solvents such as alcohol and water-containing alcohol.

Methacrylic acid is used in the copolymer in a range of 25 to 5 parts by weight, preferably in a range of from 20 to 10 parts by weight. When the content of MAA is less than said lower limit, the solubility in alkali decreases to an insufficient level, and to the contrary, when the content of MAA exceeds said upper limit, it is not preferable because in the decrease of elongation or pliability. When the content of MAA exceeds 35 parts by weight, the copolymer becomes unstable, and in order to make it stable, an emulsifying agent or a suspending agent is needed. The water resistance of the film obtained in the percentage of components of this invention is superior to that of the protective coating of the prior art.

The reason why MAA is selected instead of acrylic acid is that, aside from the fact that MAA is said to have higher safety, it was clarified to be superior in water resistance and in the reduction of residual monomers. Another important factor of selecting MAA is that it was found out that, when producing a copolymer with EA without using an emulsifying agent, an unsaturated carboxylic monomer can be used at a higher ratio when taking MAA as a polymeric constituent than when taking acrylic acid as a polymeric constituent. As a result, a safer acrylic copolymer with fewer impurities could be obtained. Comparing with the skin protective agents of the prior art, the acrylic copolymer of this invention can form a protective film which is smoother to the touch without producing a strange feeling or twitch on the skin.

Said properties required as a copolymer for skin protective can be regulated by changing the content ratio of the monomer with ethyl acrylate and methacrylic acid in acrylic copolymer. For example, when desiring a film having a particularly high water-resistance, the content of MAA should be lower, and when a film with a high solubility in alkali is intended, the content of MAA should be higher.

A general method of manufacturing an acrylic copolymer of this invention is explained below. Deionized water is heated in a closed reaction vessel which is purged with nitrogen. A persulfate, which is preliminarily dissolved in deionized water, is added as a polymerization initiator, and monomers of EA and MAA are added in a desired period while stirring. The polymerization advances, and at the time when the monomer addition ends, polymerization also comes almost to an end. In order to further decrease the residual monomer concentration, the reaction temperature should be maintained or raised higher while stirring (hereinafter, this process may be called post-treatment). By cooling the reaction solution, a desired copolymer is obtained as dispersions.

As a persulfate, ammonium persulfate, sodium persulfate and potassium persulfate are listed for example, and it can be added wholly at once, or portionwise or continuously. The amount of the persulfate should be determined at the most appropriate value depending on the polymer concentration, the polymerization temperature, polymerization duration or other conditions, but generally it is approximately 0.2 to 4 parts by weight for 100 parts by weight of the monomer, preferably approximately 0.4 to 3 parts by weight. When it is less than the lower limit, the failure in stability of the copolymer dispersion and the increase of residual monomer may be induced, and to the contrary, when it is over the upper limit, the water resistance of its coating film decreases.

In order to shorten th time required in the post-treatment, the temperature in the post treatment should be raised, or the persulfate should be additionally given in the post-treatment, or a small amount of redox catalyst such as a combinated form of hydrogen peroxide, ferrous sulfate and L-ascorbic acid should be added. If the aim is solely the completion of the polymerization and the reduction of the residual monomer, other polymerization initiators and redox catalysts than stated above may be used, but considering the application for the skin which is the aim of this invention, they are not preferable. Monomers, EA and MAA may be added separately but it is easier to add them after mixing. The speed of addition may vary, but adding them at a constant speed is preferable because the formation of coarse particles can be prevented and the temperature can be regulated easily.

The polymerization temperature should be regulated in a range of from about 45° to 98° C., preferably, from 65° to 95° C. When it is lower than the lower limit, coarse particles tend to be formed.

The copolymer concentration in the dispersion should not be specially limited but preferably 15 to 65%, and more preferably, 25 to 55%. If the concentration is below the lower limit, the necessary amount of persulfate for the monomer may increase or the relative amount of residual monomer may be increased. On the other hand, if above the upper limit, the amount of coarse particles and deposits on the vessel wall increase because the copolymer dispersions become unstable.

According to the method explained above, copolymers in a variety of degrees of polymerization can be obtained. The weight-average molecular weight is not necessarily limited, but for the purpose of this invention, it may be about 100,000 to 2,000,000, or preferably about 100,000 to 1,300,000. The molecular weight of formed copolymer can be freely selected by regulating the amount of persulfate, polymerization temperature and copolymer concentration. Or if using an alcohol such as ethanol and isopropanol as a chain transfer agent, the molecular weight can be reduced. It is not desirable to employ commonly used chain transfer agents represented by organic sulfur compounds since they are not safe for the skin.

The skin protectives of this invention can be prepared by dissolving the acrylic copolymers in an appropriate medium. An alcoholic solvent is preferable as the medium. Ethanol and water-containing ethanol are the most eligible dissolution media as a skin protective agent from the safety point of view, but if the content of ethanol is high, there are such problems as skin irritation because evaporation of the alcohol occurs too fast. To the contrary, if the water-content is high, the solubility of the copolymer is lowered or the evaporation speed falls down. Isopropanol may be preferably used in place of ethanol. A preferable mixing ratio of alcohol/water is from 60/40 to 80/20.

It is preferable to dissolve the acrylic polymer in the medium at a concentration of about 2 to 10%, preferably about 4 to 7%. If it is above the upper limit, a stretched feeling may occur or the adhesive property to the skin decreases while forming a coat. If it is below the lower limit, the formed coat film may become thin and brittle, and thus unfavorable. As a cellulose derivative to be used in this invention, methyl cellulose, ethyl cellulose and hydroxypropyl cellulose are, for example, listed. Among them, ethyl cellulose is used preferably. The loadings of these celluloses are approximately 0.3 to 2%, preferably approximately 0.7 to 1.5%. At a ratio over the upper limit, the formed coat film becomes brittle and unfavorable. Moreover, below the lower limit, it is also unfavorable because of the adhesiveness of the film while drying. The adhesiveness in coating and the strechability after drying were obviously improved by the admixture.

For the skin protective agent of this invention, it is acceptable, if desired, to mix appropriate softening agents, additives such as polyvinyl pyrrolidone, conservatives, coloring agents or pharmaceutical active ingredients. As the skin protective of this invention forms a colorless transparent thin coat film, it is very preferable from a cosmetic point of view. But depending on the purpose of use, it is allowed to design so as to be able to check for the presence of the coat film by adding appropriate coloring agents.

The package form of the skin protective, in this invention, should not be specially limited. Since the protective agent is an alcoholic solution, a closed vessel capable of preventing the volatilization of alcohol is preferable. Bottles made of glass or plastic are acceptable as well as a spray container.

Benefits of the acrylic copolymer of this invention and the advantages in manufacturing the copolymer include, among others, the following:

(1) It forms a film which hardly permits a neutral detergent to pass through, and which can be easily washed out by a weak alkaline soap.

(2) It forms a thin film having a high stretchability and excellent pliability.

(3) Almost no odor and no irritation exist when the residual monomer is 50 ppm or less. In the ordinary emulsion polymerization, much monomer is left over, and thus, the odor is strong. And to reduce the residual monomer, a long time is needed for the post-treatment because of the extension of the polymerization time. But in the polymerization method of this invention, the post-treatment is easy as the residual monomer is very little.

(4) As it is stable at ordinary temperature, it can be stored for a long period without using emulsifying agent or suspending agent.

The present invention is explained in more detail by the following Examples, which are not intended to limit the scope of the invention.

PREPARATION OF COPOLYMER

Example 1

In a closed type reaction vessel with a stirrer which was purged with nitrogen, 236.1 parts by weight of deionized water was charged, and after adjusting the temperature in the reaction vessel to 80° C., 1.2 parts by weight of ammonium persulfate was added and sequentially the following monomer mixture was added in 8 hours.

EA—85 parts by weight
MAA—15 parts by weight

Stirring was continued for another 8 hours by keeping the temperature in the reaction vessel at 80° C. to complete the reaction. The solid content of the emulsion was 30%, in which EA was contained in the amounts of 37 ppm, and MAA was less than 10 ppm according to the analysis of the residual monomer by means of gas chromatography. The mean molecular weight of this copolymer was about 840,000.

Example 2

In a closed type reaction vessel with a stirrer which was purged with nitrogen, 237.3 parts by weight of deionized water and 0.5 parts by weight of isopropanol were charged and after adjusting the temperature in the reaction vessel to 80° C., 1.7 parts by weight of ammonium persulfate was added and sequentially the following monomer mixture was added in 5 hours.

EA—85 parts by weight
MAA—15 parts by weight

By keeping the temperature in the reaction vessel at 85° C., 0.1 part by weight of hydrogen peroxide, ferrous sulfate, and L-ascorbic acid were added and stirring was continued for another 5 hours to complete the reaction. The solid content of this emulsion was 30%, in which EA was contained in the amounts of 12 ppm, and MAA was less than 10 ppm according to the analysis of the residual monomer by means of gas chromatography. The mean molecular weight of this copolymer was about 180,000.

Example 3

In a closed type reaction vessel with a stirrer which was purged with nitrogen, 237.3 parts by weight of deionized water and 2.0 parts by weight of isopropanol were charged and after adjusting the temperature in the reaction vessel to 80° C., 1.7 parts by weight of ammonium persulfate was added and sequentially the following monomer mixture was added in 8 hours.

EA—80 parts by weight
MAA—20 parts by weight

By keeping the temperature in the reaction vessel at 85° C., 0.1 part by weight of hydrogen peroxide, ferrous sulfate, and L-ascorbic acid were added and stirring was continued for another 5 hours to complete the reaction. The solid content of this emulsion was 30%, in which EA was present in an amount of 20 ppm, and MAA was less than 10 ppm according to the analysis of the residual monomer by means of gas chromatography. The mean molecular weight of this copolymer was about 130,000.

Example 4

In a closed type reaction vessel with a stirrer which was purged with nitrogen, 238.0 parts by weight of deionized water and 3.0 parts by weight of isopropanol were charged and after adjusting the temperature in the reaction vessel to 80° C., 2.0 parts by weight of ammonium persulfate was added and sequentially the following monomer mixture was added in 5 hours.

EA—75 parts by weight
MAA—25 parts by weight

By keeping the temperature in the reaction vessel at 85° C., 0.1 part by weight of hydrogen peroxide, ferrous sulfate, and L-ascorbic acid were added and stirring was continued for another 5 hours to complete the reaction. The solid content of this emulsion was 30%, in which EA was contained in an amount of 18 ppm, and MAA was less than 10 ppm according to the analysis of the residual monomer by means of gas chromatography. The mean molecular weight of this copolymer was about 110,000.

Example 5

In a closed type reaction vessel with a stirrer which was purged with nitrogen, 237.3 parts by weight of deionized water was charged and after adjusting the temperature in the reaction vessel to 80° C., 1.7 parts by weight of potassium persulfate was added and sequentially the following monomer mixture was added in 8 hours.

EA—85 parts by weight
MAA—15 parts by weight

By keeping the temperature in the reaction vessel at 80° C., 0.1 part by weight of hydrogen peroxide, ferrous sulfate, and L-ascorbic acid were added and stirring was continued for another 5 hours to complete the reaction. The solid content of this emulsion was 30%, in which EA was contained in an amount of 15 ppm, and MAA was less than 10 ppm according to the analysis of the residual monomer by means of gas chromatography. The mean molecular weight of this copolymer was about 750,000.

Example 6

In a closed type reaction vessel with a stirrer which was purged with nitrogen, 187.8 parts by weight of deionized water was charged, and after adjusting the temperature in the reaction vessel to 75° C., 1.1 parts by weight of ammonium persulfate was added and sequentially the following monomer mixture was added in 5 hours.

EA—80 parts by weight
MAA—20 parts by weight

By keeping the temperature in the reaction vessel at 88° C., 0.1 part by weight of hydrogen peroxide, ferrous sulfate, and L-ascorbic acid were added and stirring was continued for another 5 hours to complete the reaction. The solid content of this emulsion was 35%, in which EA was contained in an amount of 15 ppm, and MAA was less than 10 ppm according to the analysis of the residual monomer by means of gas chromatography. The mean molecular weight of this copolymer was about 800,000.

Example 7

In a closed type reaction vessel with a stirrer which was purged with nitrogen, 151.7 parts by weight of deionized water was charged, and after adjusting the temperature in the reaction vessel to 70° C., 1.1 parts by weight of ammonium persulfate was added and sequentially the following monomer mixture was added in 8 hours.

EA—85 parts by weight
MAA—15 parts by weight

By keeping the temperature in the reaction vessel at 80° C., 0.1 part by weight of hydrogen peroxide, ferrous sulfate, and L-ascorbic acid were added and stirring was continued for another 5 hour to complete the reaction. The solid content of this emulsion was 40%, in which EA was contained in an amount of 20 ppm, and MAA was less than 10 ppm according to the analysis of the residual monomer by means of gas chromatography. The mean molecular weight of this copolymer was about 1,180,000.

PREPARATION OF SKIN PROTECTIVE

Example 8

The emulsion prepared in Example 1 was placed in an appropriate vessel so that the copolymer content in the emulsion is 50 g. Isopropanol (hereinafter occasionally abbreviated as IP) was added in an amount of 658 g and the mixture was stirred until the polymer was dissolved perfectly. To the solution of the polymer, ethylcellulose (hereinafter sometimes abbreviated as EC) was gradually added by 10 g to prepare a solution, and water was added to make the whole 1 kg. This composition contained the polymer of the Example 1 by 5.0% and EC by 1.0% in an aqueous IP solution.

Example 9

By using the copolymer prepared in Example 2, according to the preparation method of Example 8, and aqueous IP solution containing the copolymer by 5.0% and EC in an amount of 1.0% was prepared.

Example 10

By using the copolymer prepared in Example 3, according to the preparation method of Example 8, an aqueous IP solution containing the copolymer in an amount of 5.0% and EC in an amount of 1.0% was prepared.

Example 11

By using the copolymer prepared in Example 4, according to the preparation method of Example 8, an aqueous IP solution containing the copolymer in an amount of 5.0% and EC in an amount of 1.0% was prepared.

Example 12

By using the copolymer prepared in Example 1, according to the preparation method of Example 8, an aqueous IP solution containing the copolymer in an amount of 3.5% and EC in an amount of 1.0% was prepared.

Example 13

By using the copolymer prepared in Example 1, according to the preparation method of Example 8, an aqueous IP solution containing the copolymer in an amount of 7.0% and EC in an amount of 1.0% was prepared.

Example 14

By using the copolymer prepared in Example 1, according to the preparation method of Example 8, an aqueous IP solution containing the copolymer in an amount of 10.0% and EC in an amount of 1.0% was prepared.

Example 15

By using the copolymer prepared in Example 2, according to the preparation method of Example 8, an aqueous IP solution containing the copolymer in an amount of 7.0% and EC in an amount of 1.0% was prepared.

Experiment 1

The property of the acrylic copolymer of this invention was examined by applying the following compositions on the back of the human hand. The results are shown in Table 1.

COPOLYMER TESTED

Composition 1 (Invention):

To 26.4 parts by weight of emulsion prepared in Example 1, 65.4 parts by weight of isopropanol was added, and 9.2 parts by weight of purified water was added to prepare the solution for skin protection.

Composition 2 (Invention):

To 26.4 parts by weight of emulsion prepared in Example 4, 65.4 parts by weight of isopropanol was added and 9.2 parts by weight of purified water was added to prepare the solution for skin protection.

Composition 3 (Invention):

To 22.8 parts by weight of emulsion prepared in Example 6, 64.4 parts by weight of ethanol was added and 12.8 parts by weight of purified water was added to prepare the solution for skin protection.

Reference Composition 1 (Prior Art):

Eudragit L30D-55 (acrylic copolymer made by Röhm Pharma, West Germany; concentration of solid content—30%) was dissolved in 64.4 parts by weight of isopropanol by 26.4 parts by weight, and 9.2 parts by weight of purified water was added to prepare the solution for skin protective.

The following component was contained in an aqueous IP solution.
Copolymer of Example 1: 5.0%

Composition 6

The following component was contained in an aqueous IP solution.
Copolymer of Example 1: 7.0%

Composition 7

The following component was contained in an aqueous IP solution.
Copolymer of Example 1: 10.0%

Prior Art Composition 1

The following component was contained in an aqueous IP solution.
Eudragit E30D: 5.0%
EC: 1.0%

Prior Art Composition 2

The following component was contained in an aqueous IP solution.
Eudragit E30D: 10.0%
EC: 1.0%

TABLE 1

| Sample Tested | Adhesiveness | Transparence | Spreadability | Contractility (Stiffness) | Water-Resistance | Solubility in Alkali | Permeability of Moisture | Overall Evaluation |
|---|---|---|---|---|---|---|---|---|
| Composition 1 | O | O | O | O | O | O | O | O |
| Composition 2 | O | O | O | O | O | O | O | O |
| Composition 3 | O | O | O | O | O | O | O | O |
| Ref. Comp. 1 | X | O | X | O | O | O | O | X |

(Note)
O: Good,
X: Not Good

Experiment 2

The property of the composition of this invention was examined by applying the following compositions on the back of the human hand. As references, an EC-free composition of the polymer of this invention, a composition with a known acrylic polymer and a commercial liquid adhesive plaster were used. The results are shown in Table 2.

COMPOSITION TESTED

Test Compositions (The Present Invention):
Compositions prepared in Examples 8 to 14
Composition (including Prior Arts)

Composition 4

The following component was contained in an aqueous IP solution.
Copolymer of Example 1: 3.5%

Composition 5

Prior Art Composition 3

The following component was contained in an aqueous IP solution.
Eudragit L30D-55: 10.0%
EC: 1.0%

Prior Art Composition 4

A commercially available film forming composition (aerosol type).

Prior Art Composition 5

A commercially available liquid adhesive plaster.

RESULTS

The skin protective agent of this invention showed obviously high organoleptic characteristics compared with a skin protective agent using a known acrylic polymer and a liquid adhesive plaster sold in the market. Moreover, the adhesive property in coating and the spreadability after drying were improved by the addition of cellulose.

TABLE 2

| | | When Applied | | After Dried | | | | |
|---|---|---|---|---|---|---|---|---|
| Sample Tested | | Adhesiveness | Stickiness | Adhesiveness | Transparence | Stretchablity | Stiffness | Overall Evaluation |
| INVENTION | Example 8 | O | O | O | O | O | O | O |
| | Example 9 | O | O | O | O | O | O | O |
| | Example 10 | O | O | O | O | O | O | O |
| | Example 11 | O | O | O | O | O | O | O |
| | Example 12 | O | O | O | O | O | O | O |
| | Example 13 | O | O | O | O | O | O | O |
| | Example 14 | O | O | O | O | O | O | O |
| EC-free | Comp. 4 | Δ | Δ | Δ | O | O | O | Δ |
| | Comp. 5 | O | Δ | O | O | Δ | O | O |
| | Comp. 6 | O | Δ | O | O | Δ | O | O |
| | Comp. 7 | Δ | Δ | O | O | Δ | Δ | Δ |

TABLE 2-continued

| Sample Tested | | When Applied | | After Dried | | | | Overall Evaluation |
|---|---|---|---|---|---|---|---|---|
| | | Adhesiveness | Stickiness | Adhesiveness | Transparence | Stretchablity | Stiffness | |
| Prior Art | Prior Comp. 1 | O | Δ | O | O | Δ | O | O |
| | Prior Comp. 2 | O | X | O | O | Δ | Δ | Δ |
| | Prior Comp. 3 | X | O | Δ | O | X | O | X |
| | Prior Comp. 4 | O | Δ | O | Δ | X | X | X |
| | Prior Comp. 5 | O | O | O | Δ | X | X | X |

(Note)
O: Good,
Δ: Even,
X: Not Good

Experiment 3

The organoleptic examination was performed on seven healthy adults by using the skin protective agent of the present invention. The test method is stated below.

Application of the Composition Tested

According to the following criteria, the composition was applied on the right hand and the test composition on the left hand.

1. Five drops (approximately 100 mg) of a composition were put on the back of the right hand.
2. By using fingertips of the left hand, those drops were evenly spread from the center of the back of the right hand to the second joints of the four fingers.
3. Five drops (approximately 100 mg) of test composition were put on the back of the left hand.
4. By using fingertips of the right hand, those drops were evenly spread from the center of the back of the left hand to the second joints of the four fingers.
5. The state immediately after coating was evaluated.
6. The dry state of the composition was evaluated 10 minutes after dropping.
7. Sequentially, the state after using water was evaluated.
8. The compositions were removed by 70% ethanol.
9. Regarding the items 1 to 8 as one course, three courses a day were done for evaluation. Each interval between the neighboring courses should be longer than three hours.

Items and Criteria for Evaluation

Evaluation items
Immediately after Application
 1. Easiness to spread
 2. Stickiness
 3. Easiness to dry
 4. Total evaluation just after applied
After drying
 5. Gloss of the film formed
 6. Smoothness of the film
 7. Resistance to peeling-off
 8. Twitch feeling to the skin
 9. Total evaluation after drying
When using water
 10. Resistance to peeling-off
 11. Sliminess
 12. Total evaluation when using water
Overall Evaluation
 13. Overall evaluation throughout the above items.
Evaluation Criteria Scores stated below were given on the respective items above, and analyzed according to the balance type incomplete block design.

Score

Poor: −2, Slightly Poor: −1, Even: 0, Slightly Good: +1, Good: +2.

According to the test method explained above, the organoleptic properties were compared on the compositions below. The results are shown in Table 3, where the scored values in the following tables indicate that, if it is larger than 0, the value is higher than the reference composition and to the contrary, if it is smaller than 0, the value is lower.

(Composition Tested)
Present Invention:
Skin-protectives prepared in Examples 8 and 9
Prior Art:
Prior Art Composition 6, containing the following components in aqueous IP solution.
 Eudragit E30D: 3.5%
 EC: 1.5%
Prior Art Composition 7, containing the following components in aqueous IP solution.
 Eudragit L30D-55: 5.0%
 Propylene glycol: 1.0%

TABLE 3

| | Composition Tested | | | |
|---|---|---|---|---|
| | Invention | | Prior Art | |
| Test Items | Example 8 | Example 9 | Prior Art 6 | Prior Art 7 |
| 1 | 0.095 | 0.381 | 0.095 | 0.238 |
| 2 | −0.143 | 0.714 | −0.143 | 0.286 |
| 3 | 0.048 | 0.333 | 0.047 | −0.381 |
| 5 | −0.095 | 0.048 | 0.048 | 0.048 |
| 7 | −0.048 | −0.048 | −0.333 | −0.048 |
| 8 | 0.095 | 0.952 | 0.952 | 0.381 |
| 13 | 0.095 | 0.476 | −0.095 | 0.048 |

Results

The skin protective of this invention showed high organoleptic characteristics comparing with a skin protective using known acrylic copolymer.

Experiment 4

According to the method stated in Experiment 3, a preferable concentration of the copolymer in the skin protective was examined. The results are shown in Table 4.

Composition Tested
 Example 9: copolymer 5.0%
 Example 15: copolymer 7.0%

TABLE 4

| | Composition Tested | |
|---|---|---|
| Test Items | Example 9 | Example 15 |
| 1 | 0.458 | 0.167 |
| 2 | 0.025 | −0.267 |
| 3 | 0.000 | 0.125 |
| 4 | 0.300 | −0.117 |
| 5 | 1.000 | 0.292 |
| 6 | 0.208 | −0.167 |

TABLE 4-continued

| Test Items | Composition Tested | |
|---|---|---|
| | Example 9 | Example 15 |
| 7 | 0.008 | −0.033 |
| 8 | 0.733 | −0.017 |
| 9 | 0.442 | −0.183 |
| 10 | −0.192 | −0.108 |
| 11 | −0.158 | −0.200 |
| 13 | 0.358 | −0.100 |

Results

The preferable concentration of the copolymer was 5%.

Effects of the invention

The skin protective agents of this invention mainly made of an acrylic copolymer were proven to have a higher safety and better feeling than any others of the prior art. The skin protective agent of the present invention forms a very thin coat film by applying only a very small amount on the skin. The formed coat film has sufficient waterproof properties, is stretchable and pliable, and adheres tightly to the skin without giving a strange feeling. Besides, because they contain substantially no surfactant and because the amount of residual monomer is kept to a minimum, it is less irritating to the skin and can prevent neutral detergents from passing through, and it is, hence, highly safe. And at the same time, after use, it can be easily removed by an alcohol or weak alkaline solutions such as a soap. It can therefore provide an excellent hand protective coat film for housewives, professional dishwashers, chemical workers, mechanics, and others.

Moreover, if an appropriate external skin agent is applied before using the skin protective of this invention, it can be useful as a liquid adhesive plaster or a protective coat in ODT treatment, especially helpful for the locations contracted and expanded severely including hand, the elbow, neck, face and the like.

What is claimed is:

1. A skin-protective composition consisting essentially of an effective skin-protective amount of an acrylic copolymer of ethyl acrylate and methacrylate acid in which the ratio of ethyl acrylate to methacrylic acid is within a range of 75:25 and 95:5 and which contains residual monomers of 50 ppm or less, but substantially no surfactants and an alcoholic solvent.

2. A skin-protective agent according to claim 1 in which the alcoholic solvent is a mixture of water and alcohol.

3. A skin protective agent according to claim 2 in which the alcoholic solvent contains water and alcohol in an alcohol/water ratio of from 60:40.

4. A composition according to claim 3 in which the alcohol is selected from the group consisting of ethanol and isopropanol.

5. A skin-protective composition according to claim 4 in which the acrylic polymer is present in an amount of from about 2 to 10%.

6. A skin-protective composition according to claim 1 which also contains a cellulose derivative.

7. A skin-protective composition according to claim 6 in which the cellulose derivative is selected from the group consisting of methylcellulose, ethylcellulose and hydroxypropyl cellulose.

8. A skin-protective composition according to claim 7 in which the cellulose derivative is present in an amount of 0.3 to 2.0%.

9. A skin-protective composition according to claim 8 which also contains conventional additive for the skin selected from the group consisting of softening agents, conservatives and colony agents.

10. A skin-protective composition consisting essentially of the following components:
   a. an acrylic copolymer of ethyl acrylate and methacrylic acid wherein the weight ratio of ethyl acrylate to methacrylic acid in a range between 75:25 and 95:5, said copolymer containing therein residual monomer(s) at 50 ppm or less, but substantially no surfactants—approximately 2 to 10%;
   b. a cellulose derivative—approximately 0.2 to 2%; and
   c. a necessary amount of aqueous alcohol to make the whole 100%.

11. A skin-protective composition according to claim 10 in which the weight-average molecular weight of the acrylic copolymer is between about 100,000 and about 2,000,000.

12. A skin-protective composition according to claim 10 in which the weight-average molecular weight of the acrylic copolymer is between about 100,000 and about 1,300,000.

13. A skin-protective composition according to claim 10 in which the cellulose derivative is selected from the group consisting of methylcellulose, ethylcellulose and hydroxypropyl cellulose.

14. A skin-protective agent according to claim 13 in which the alcohol present in the aqueous alcohol mixture is ethanol or isopropanol.

15. A skin-protective agent according to claim 14 in which the mixing ratio of the alcohol/water is 60/40.

16. A method of forming a skin-protective coating on the skin which comprises applying to the skin, in sufficient amounts to form on a coating on the skin, a skin-protective composition according to claim 1.

17. A method of forming a skin-protective coating on the skin which comprises applying to the skin, in sufficient amounts to form on a coating on the skin, a skin-protective composition according to claim 10.

* * * * *